US00PP34619P3

(12) United States Plant Patent
Olesen

(10) Patent No.: US PP34,619 P3
(45) Date of Patent: Oct. 4, 2022

(54) COMPACT FLORIBUNDA ROSE PLANT NAMED 'POULCAS069'

(50) Latin Name: *Rosa hybrida*
Varietal Denomination: 'Poulcas069'

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,613

(22) Filed: Sep. 7, 2021

(65) Prior Publication Data

US 2022/0095511 P1 Mar. 24, 2022

(30) Foreign Application Priority Data

Sep. 21, 2020 (QZ) ..... 2020/2245

(51) Int. Cl.
*A01H 5/02* (2018.01)
*A01H 6/74* (2018.01)

(52) U.S. Cl.
USPC ..... Plt./150
CPC ..... *A01H 6/749* (2018.05)

(58) Field of Classification Search
USPC ..... Plt./149, 150, 151
CPC ..... A01H 5/0222
See application file for complete search history.

(56) References Cited

PUBLICATIONS https://www.poulsenroser.dk/en/roses/ShowProduct/63329; Oct. 8, 2021; 2 pages.*

* cited by examiner

*Primary Examiner* — Kent L Bell

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulcas069'.

This application claims priority to Plant Breeder's Rights Application Number 2020/2245, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulcas069', originated as a single seedling from the stated cross.

The new variety may be distinguished from its male pollen parent and female seed parent primarily by the following characteristics. The male pollen parent plant has a growth height of less than 50 cm, while the new variety has a growth height of 55 cm to 75 cm in one growing season. The female seed parent plant has light pink flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcas069' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulcas069' was selected in the spring of 2013 by the inventor as a single plant from the progeny of the aforementioned hybridization.

Asexual reproduction of 'Poulcas069' by rooted cuttings was first done by Mogens N. Olesen in the nursery in Fredensborg, Denmark in July, 2013. This initial and other subsequent asexual propagations conducted in controlled environments have demonstrated that the characteristics of 'Poulcas069' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas069'.

Specifically illustrated in FIG. 1 of the drawings are flower buds, open flowers with petals detached, showing reproductive flower parts sepals, and receptacle.

Figure 1:
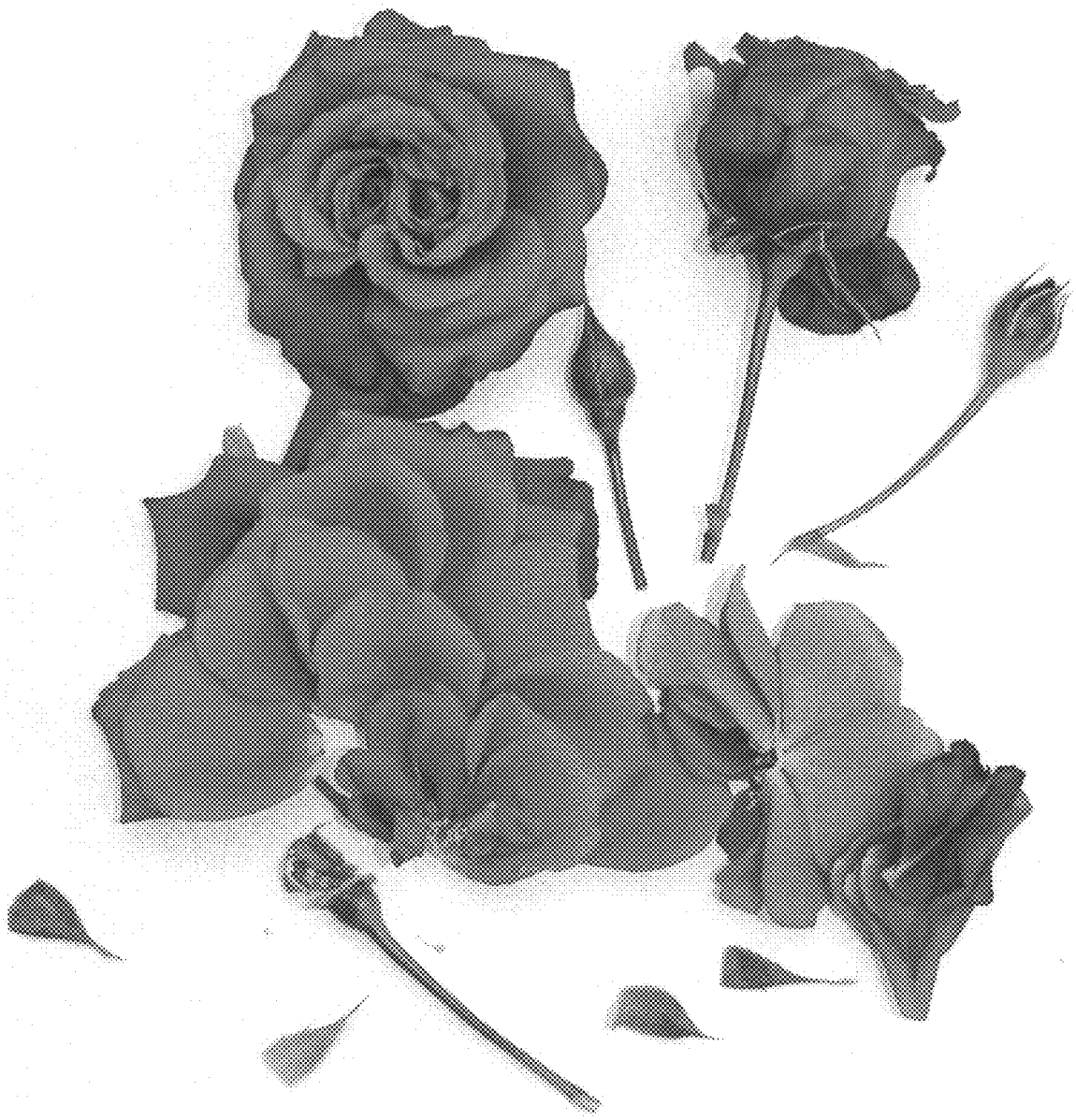
Figure 2:
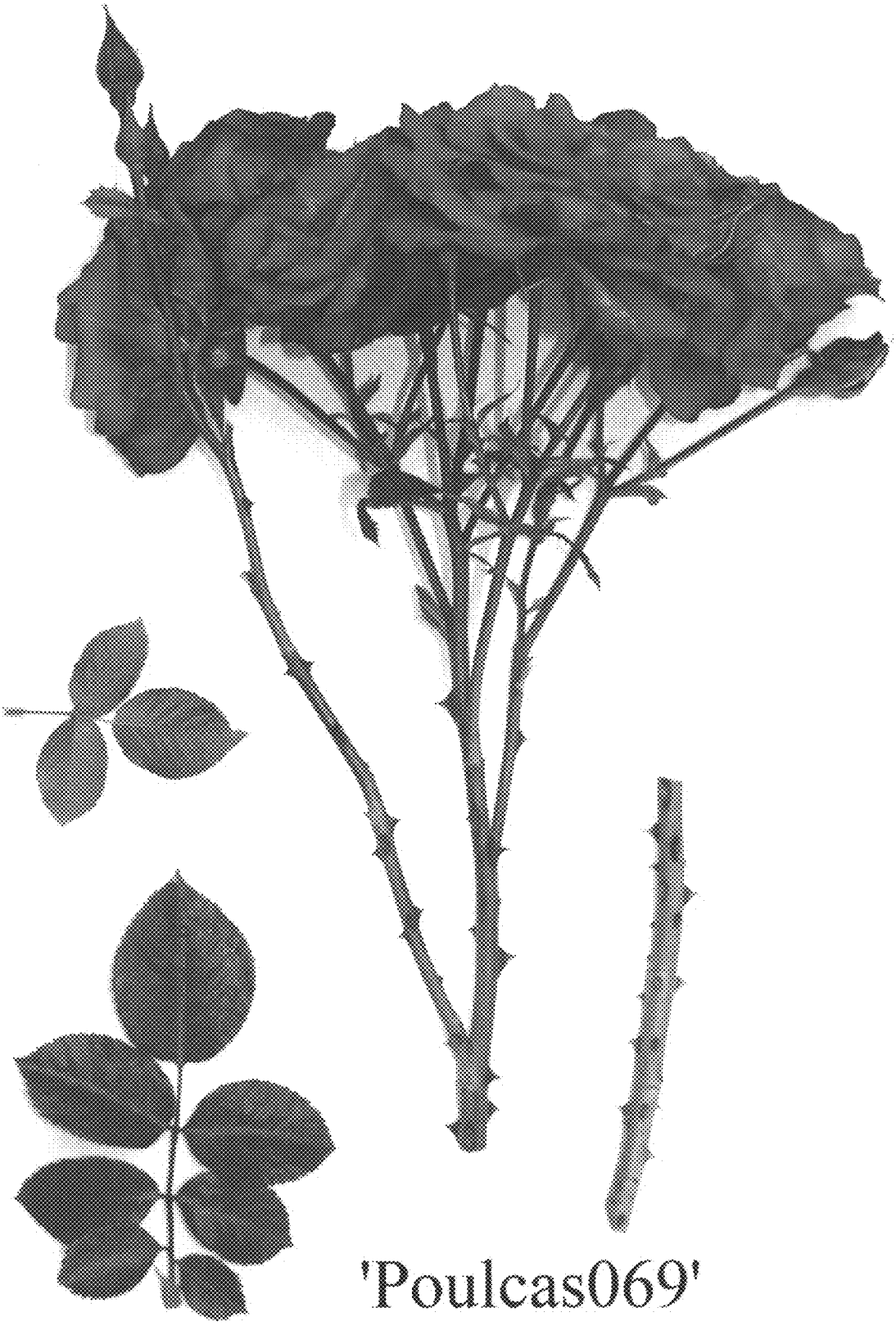

Specifically illustrated in FIG. 2 of the drawings is a cluster of open flowers on the branch showing peduncles and inflorescence arrangement, leaves and bare stems. Plants shown are 2 years of age.

DETAILED DESCRIPTION OF THE VARIETY

The following is a description of 'Poulcas069', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas034', U.S. Plant Pat. No. 24,225 are compared to 'Poulcas069' in Chart 1.

CHART 1

| | 'Poulcas069' | 'Poulcas034' |
|---|---|---|
| Petal Count | 43 | 70 |
| Flower Diameter | 75 mm | 90 to 100 mm |
| General Tonality of Flower Color | Red Group 53A and Red-Purple Group N57A | Red Group 45B |

FLOWER AND FLOWER BUD

Blooming habit: Continuous.

Flower bud:

*Size*.—Upon opening, 30 mm in length from base of receptacle to end of bud. Bud diameter is 15 mm.

*Bud form*.—Ovoid.

*Bud color*.—As sepals divide petals are Red Group 53A.

*Sepal inner surface*.—Color: Yellow-Green Group 146D. Surface: Lightly pubescent.

*Sepal outer surface*.—Color: Yellow-Green Group 144A with strong intonations of Greyed-Purple Group 183A. Texture: Smooth.

*Sepal shape*.—Generally subulate. Apex: Cirrhose. Base: Flat at union with receptacle.

*Sepal margin*.—Margins have weak foliaceous appendages on three of the five sepals.

*Sepal size*.—16 mm long, 10 mm wide.

*Receptacle*.—Texture: Smooth. Size: 5 mm in height, 7 mm wide. Color: Yellow-Green Group 144A with intonations of Greyed-Purple Group 183B. Shape: Campanulate.

*Pedicel*.—Surface: Smooth. Length: 45 mm. Diameter: 2 mm on average. Color: Yellow-Green Group 144B with intonations of Greyed-Purple Group 183C. Strength: Strong.

*Peduncle*.—Length: 2 to 9 cm. Texture: Smooth. Diameter: About 4 to 5 mm. Color: Yellow-Green Group 144A with intonations of Greyed-Purple Group 183A. Texture: Smooth.

Flower bud development: Flower buds are borne in clusters of 5 up to 15 flower buds per stem. Development as a panicle.

Flower bloom:

*Fragrance*.—Strong rose perfume.

*Duration*.—The blooms have a duration on the plant of approximately 14 days. Petals fall cleanly away from plant after flowers have fully matured.

*Size*.—Flower diameter is 75 mm when open. Flower depth is 38 mm.

*Flower shape*.—Deep cup, with petals arranged in quarter sections.

*Shape of flower, side view*.—The upper portion is flat. The lower portion is flat concave.

Petalage: Under normal conditions, flowers have about 43 petals.

General tonality of flower: Open flowers are Red Group 53A and Red-Purple Group N57A.

Petal color:

*Upon opening, outer petals*.—Upper surface: Red-Purple Group N57A with intonations of Red-Purple Group N59A. Lower surface: Red-Purple Group 61B.

*Upon opening, inner petals*.—Upper surface: Red-Purple Group N57A with intonations of Red-Purple Group N59A. Lower surface: Red-Purple Group 61B.

*Basal petal spots, upon opening*.—Upper surface: Yellow Group 4A. Lower surface: Yellow Group 4A.

*After opening, outer petals*.—Upper surface: Red-Purple Group N57A with intonations of Red-Purple Group N59A. Lower surface: Red-Purple Group 61B.

*After opening, inner petals*.—Upper surface: Red-Purple Group N57A with intonations of Red-Purple Group N59A. Lower surface: Red-Purple Group 61B.

*Basal petal spots, after opening*.—Upper surface: Yellow Group 4A. Lower surface: Yellow Group 4A.

Petals:

*Petal reflex*.—Slightly reflexed.

*Margin*.—Entire and uniform with minor undulations.

*Shape*.—Broad and elliptic. Apex shape: Rounded. Base shape: Acute.

*Size*.—50 mm (l)×54 mm (w).

*Texture*.—Smooth.

*Thickness*.—Average.

Petaloids:

*Size*.—15 mm (l) by 10 mm (w).

*Quantity*.—About 10.

*Shape*.—Elliptical with an acute base and rounded apices.

*Color*.—Red-Purple Group N57A with intonations of Red-Purple Group N59A on the upper surface. The lower surface is Red-Purple Group 16B, with a petal spot of Yellow 4A on both sides.

Reproductive flower parts:

*Pollen*.—None observed.

*Anthers*.—Size: 2 mm in length. Color: Yellow Group 4B. Quantity: 42 on average.

*Filaments*.—Color: Greyed-Orange Group 171A. Length: 8 mm.

*Pistils*.—Length: 8 mm. Quantity: 30 on average.

*Stigmas*.—Color: Orange-White Group 158A.

*Styles*.—Color: Red-Purple Group 61D.

*Location of stigmas*.—Level in location relative to the length of the filaments and the height of the anthers.

*Hips*.—None Observed.

PLANT

Plant growth: Upright, bushy. Plants are 55 cm to 75 cm in height, and 45 cm wide.

Stems:

*Color of juvenile growth*.—Yellow-Green Group 144A with intonations of Greyed-Purple Group 183C.

*Color of mature growth*.—Yellow-Green Group 144A.

*Length*.—Canes are about 30 cm from the base of the plant to the flowering portion.

*Diameter*.—About 10 mm.

*Internodes*.—On mature canes about 30 to 40 mm between nodes.

*Surface texture*.—Young wood: Smooth. Older wood: Smooth.

Long prickles:

*Incidence*.—13 prickles per 10 cm of stem.

*Size*.—Average length of prickles on mature stems is 8 mm.

*Shape*.—Upper portion is concave. Lower portion is concave.

*Color*.—Juvenile prickles: Greyed-Purple Group 184A. Mature prickles: Greyed-Purple Group 184A with other intonations of Greyed-Orange Group N170B.

Plant foliage:

*Compound leaf*.—145 mm (l)×100 mm (w).

*Quantity*.—2 leaves per 10 cm of stem on average.

*Leaf bearing angle to the stem*.—45 degrees.

*Color of juvenile foliage*.—Upper side: Yellow-Green Group 144A shaded with Greyed-Red Group 178B. Lower side: Yellow-Green Group 144A shaded with Greyed-Red Group 178B.

*Color of mature foliage*.—Upper side: Yellow-Green Group 147A. Lower side: Yellow-Green Group 146B.

Plant leaves and leaflets:

*Stipules*.—Size: 20 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 1.5 mm. Upper surface color: Yellow-Green Group 144A with intonations of Greyed-Purple Group 183B. Lower surface color: Yellow-Green Group 144A.

*Rachis*.—Length: 50 mm. Diameter: 2 mm. Upper surface color: Yellow-Green Group 144A with intonations of Greyed-Purple Group 183B. Lower surface color:

*Leaflet*.—Quantity: Normally 5 or 7 leaflets. Juvenile leaves are occasionally trifoliate. Margins: Serrated. Size: Terminal leaflets are about 60 mm long, 41 mm wide. Shape: Generally elliptical. Base: Rounded. Apex: Mucronate. Texture: Smooth. Thickness: Above average. Arrangement: Odd pinnate. Venation: Reticulate. Glossiness: Glossy.

Disease resistance: Above average resistance to powdery mildew *Sphaerotheca pannosa* var. *rosae,* downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety is susceptible to any insect pest normally associated with the species.

I claim:

1. A new and distinct variety of rose plant of the Compact Floribunda rose class named 'Poulcas069', substantially as illustrated and described herein, due to its abundant red flowers, disease resistance, and extended period of bloom.

* * * * *

'Poulcas069'

'Poulcas069'